United States Patent
Burbank et al.

(10) Patent No.: US 7,322,939 B2
(45) Date of Patent: *Jan. 29, 2008

(54) BREAST BIOPSY SYSTEM AND METHODS

(75) Inventors: Fred H. Burbank, San Juan Capistrano, CA (US); Michael L. Jones, Capistrano Beach, CA (US); Paul Lubock, Laguna Niguel, CA (US)

(73) Assignee: Senorx, Inc.

( * ) Notice: Subject to any disclaimer, the term of this patent is extended or adjusted under 35 U.S.C. 154(b) by 353 days.

This patent is subject to a terminal disclaimer.

(21) Appl. No.: 10/719,612

(22) Filed: Nov. 21, 2003

(65) Prior Publication Data

US 2004/0153004 A1 Aug. 5, 2004

Related U.S. Application Data

(60) Continuation of application No. 09/929,371, filed on Aug. 13, 2001, which is a division of application No. 09/057,303, filed on Apr. 8, 1998, now Pat. No. 6,331,166.

(60) Provisional application No. 60/076,973, filed on Mar. 3, 1998.

(51) Int. Cl.
*A61B 10/00* (2006.01)
*A61B 18/18* (2006.01)

(52) U.S. Cl. .......................... 600/564; 606/45

(58) Field of Classification Search ........ 600/562–567; 606/114, 41, 45–52; 604/23, 114
See application file for complete search history.

(56) References Cited

U.S. PATENT DOCUMENTS

| | | |
|---|---|---|
| 2,032,860 A | 3/1936 | Wappler et al. |
| 3,805,791 A | 4/1974 | Seuberth et al. |

(Continued)

FOREIGN PATENT DOCUMENTS

DE 19528440 A1 8/1995

(Continued)

OTHER PUBLICATIONS

Armstrong, J.S. et al., "Differential marking of excision planes in screened breast lesions by organically coloured gelantins (see comments)", *Journal of Clinical Pathology*, (Jul. 1990), 43 (7) 604-7, XP000971447 abstract; tables 1 & 2.

(Continued)

*Primary Examiner*—Max F. Hindenburg
*Assistant Examiner*—Brian Szmal
(74) *Attorney, Agent, or Firm*—Edward J. Lynch (57) ABSTRACT

An apparatus and method are provided for precisely isolating a target lesion in a patient's body tissue, resulting in a high likelihood of "clean" margins about the lesion when it is removed for diagnosis and/or therapy. This approach advantageously will often result in the ability to both diagnose and treat a malignant lesion with only a single percutaneous procedure, with no follow-up percutaneous or surgical procedure required, while minimizing the risk of migration of possibly cancerous cells from the lesion to surrounding tissue or the bloodstream. In particular, the apparatus comprises a biopsy instrument having a distal end adapted for entry into the patient's body, a longitudinal shaft, and a cutting element disposed along the shaft. The cutting element is actuatable between a radially retracted position and a radially extended position. Advantageously, the instrument is rotatable about its axis in the radially extended position to isolate a desired tissue specimen from surrounding tissue by defining a peripheral margin about the tissue specimen. Once the tissue specimen is isolated, it may be segmented by further manipulation of the cutting element, after which the tissue segments are preferably individually removed from the patient's body through a cannula or the like. Alternatively, the specimen may be encapsulated and removed as an intact piece.

23 Claims, 11 Drawing Sheets

U.S. PATENT DOCUMENTS

| | | |
|---|---|---|
| 3,844,272 A | 10/1974 | Banko |
| 3,945,375 A | 3/1976 | Banko et al. |
| 3,955,578 A | 5/1976 | Chamness et al. |
| 4,202,338 A | 5/1980 | Bitrolf |
| 4,294,254 A | 10/1981 | Chamness |
| 4,311,143 A | 1/1982 | Komiya |
| 4,362,160 A | 12/1982 | Hiltebrandt |
| 4,503,855 A | 3/1985 | Maslanka |
| 4,532,924 A | 8/1985 | Auth et al. |
| 4,576,162 A | 3/1986 | McCorkle |
| 4,638,802 A | 1/1987 | Okada |
| 4,718,419 A | 1/1988 | Okada |
| 4,724,836 A | 2/1988 | Okada |
| 5,007,908 A | 4/1991 | Rydell |
| 5,024,617 A | 6/1991 | Karpiel |
| 5,035,696 A | 7/1991 | Rydell |
| 5,064,424 A | 11/1991 | Bitrolf |
| 5,066,295 A | 11/1991 | Kozak et al. |
| 5,078,716 A | 1/1992 | Doll |
| 5,080,660 A | 1/1992 | Buelna |
| 5,085,659 A | 2/1992 | Rydell |
| 5,158,561 A | 10/1992 | Rydell et al. |
| 5,163,938 A | 11/1992 | Kambara et al. |
| 5,196,007 A | 3/1993 | Ellman et al. |
| 5,201,732 A | 4/1993 | Parins et al. |
| 5,201,741 A | 4/1993 | Dulebohn |
| 5,207,686 A | 5/1993 | Dolgin |
| 5,224,488 A | 7/1993 | Neufer |
| 5,311,858 A | 5/1994 | Adair |
| 5,312,400 A | 5/1994 | Bales et al. |
| 5,318,564 A | 6/1994 | Eggers |
| 5,323,768 A | 6/1994 | Saito et al. |
| 5,324,288 A | 6/1994 | Billings et al. |
| 5,335,671 A | 8/1994 | Clement |
| 5,344,420 A | 9/1994 | Hilal et al. |
| 5,376,094 A | 12/1994 | Kline |
| 5,380,321 A | 1/1995 | Yoon |
| 5,395,312 A | 3/1995 | Desai |
| 5,397,320 A | 3/1995 | Essig et al. |
| 5,415,656 A | 5/1995 | Tihon et al. |
| 5,417,697 A | 5/1995 | Wilk et al. |
| 5,423,814 A | 6/1995 | Zhu et al. |
| 5,437,665 A | 8/1995 | Munro |
| 5,441,503 A | 8/1995 | Considine et al. |
| 5,462,553 A | 10/1995 | Dolgin |
| 5,484,436 A | 1/1996 | Eggers et al. |
| 5,501,654 A | 3/1996 | Failla et al. |
| 5,501,694 A | 3/1996 | Ressemann et al. |
| 5,526,822 A | 6/1996 | Burbank et al. |
| 5,542,948 A | 8/1996 | Weaver et al. |
| 5,549,108 A | 8/1996 | Edwards et al. |
| 5,595,185 A | 1/1997 | Erlich et al. |
| 5,611,803 A | 3/1997 | Heaven et al. |
| 5,643,282 A | 7/1997 | Kieturakis |
| 5,649,547 A | 7/1997 | Ritchart et al. |
| 5,665,085 A | 9/1997 | Nardella |
| 5,674,184 A | 10/1997 | Hassler, Jr. |
| 5,683,384 A | 11/1997 | Gough et al. |
| 5,769,086 A | 6/1998 | Ritchart et al. |
| 5,794,626 A | 8/1998 | Kieturakis |
| 5,810,764 A * | 9/1998 | Eggers et al. ................. 604/23 |
| 5,941,869 A | 8/1999 | Patterson et al. |
| 5,980,469 A | 11/1999 | Burbank et al. |
| 6,280,450 B1 * | 8/2001 | McGuckin, Jr. ............ 606/114 |
| 6,331,166 B1 | 12/2001 | Burbank et al. |
| 6,454,727 B1 | 9/2002 | Burbank et al. |
| 6,494,881 B1 | 12/2002 | Bales et al. |
| 6,514,248 B1 | 2/2003 | Eggers et al. |
| 6,540,695 B1 | 4/2003 | Burbank et al. |
| 6,689,145 B2 | 2/2004 | Lee et al. |
| 6,699,206 B2 | 3/2004 | Burbank et al. |
| 6,712,775 B2 | 3/2004 | Burbank et al. |
| 2003/0004407 A1 | 1/2003 | Carroll et al. |

FOREIGN PATENT DOCUMENTS

| | | |
|---|---|---|
| EP | 0 472 368 A2 | 8/1991 |
| EP | 0 970 658 | 1/2001 |
| GB | 2311468 A | 1/1997 |
| WO | PCT/GB94/01536 | 7/1994 |
| WO | PCT/GB94/01537 | 7/1994 |
| WO | 95/02371 | 1/1995 |
| WO | WO 02/22023 | 3/2002 |
| WO | WO 2005/063126 | 7/2005 |

OTHER PUBLICATIONS

"The Loop Electrode: a New Device for US-guided Interstitial Tissue Ablation Using Radio frequency Electrosurgery—An Animal Study" 1996 Blackwell Science Ltd. *Min Incas Ther & Allied Technol*, pp. 5, 511-516.

International Search Report for PCT/US2005/027071 mailed Mar. 21, 2006.

* cited by examiner

BREAST BIOPSY SYSTEM AND METHODS

RELATED APPLICATIONS

This application is a continuation of application Ser. No. 09/929,371, filed Aug. 13, 2001,which is a divisional of application Ser. No. 09/057,303, filed Apr. 8, 1998, now U.S. Pat. No. 6,331,166, which is a continuation of provisional application Ser. No. 60/076,973, filed on Mar. 3, 1998, which are incorporated herein in their entireties by reference and which priorities are claimed.

FIELD OF THE INVENTION

The present invention relates to methods and devices for removing tissue samples, and more specifically to improved instruments and methods for acquiring soft body tissue.

BACKGROUND OF THE INVENTION

It is often desirable and frequently necessary to sample or remove a portion of tissue from humans and other animals, particularly in the diagnosis and treatment of patients with cancerous tumors, pre-malignant conditions, and other diseases or disorders.

Typically, in the case of cancer, particularly cancer of the breast, there is a great emphasis on early detection and diagnosis through the use of screening modalities, such as physical examination, and particularly mammography, which is capable of detecting very small abnormalities, often nonpalpable. When the physician establishes by means of a mammogram or other screening modality, such as ultrasound, that suspicious circumstances exist, a biopsy must be performed to capture tissue for a definitive diagnosis as to whether the suspicious lesion is cancerous. Biopsy may be done by an open or percutaneous technique. Open biopsy, which is an invasive surgical procedure using a scalpel and involving direct vision of the target area, removes the entire mass (excisional biopsy) or a part of the mass (incisional biopsy). Percutaneous biopsy, on the other hand, is usually done with a needle-like instrument through a relatively small incision, blindly or with the aid of an artificial imaging device, and may be either a fine needle aspiration (FNA) or a core biopsy. In FNA biopsy, individual cells or clusters of cells are obtained for cytologic examination and may be prepared such as in a Papanicolaou smear. In core biopsy, as the term suggests, a core or fragment of tissue is obtained for histologic examination which may be done via a frozen section or paraffin section.

The type of biopsy utilized depends in large part on circumstances present with respect to the patient, including the location of the lesion(s) within the body, and no single procedure is ideal for all cases. However, core biopsy is extremely useful in a number of conditions and is being used more frequently by the medical profession.

A very successful type of image guided percutaneous core breast biopsy instrument currently available is a vacuum-assisted automatic core biopsy device. One such successful biopsy device is shown and disclosed in U.S. Pat. No. 5,526,822 to Burbank et al, expressly incorporated by reference herein. This device, known commercially as the MAMMOTOME® Biopsy System, which is available from Ethicon Endo-Surgery, Inc., a division of Johnson & Johnson, has the capability to actively capture tissue prior to cutting the tissue. Active capture allows for sampling through non-homogeneous tissues. The device is comprised of a disposable probe, a motorized drive unit, and an integrated vacuum source. The probe is made of stainless steel and molded plastic and is designed for collection of multiple tissue samples with a single insertion of the probe into the breast. The tip of the probe is configured with a laterally disposed sampling notch for capturing tissue samples. Orientation of the sample notch is directed by the physician, who uses a thumbwheel to direct tissue sampling in any direction about the circumference of the probe. A hollow cylindrical cutter severs and transports tissue samples to a tissue collection chamber for later testing.

While this type of system functions very well as a core biopsy device, there are occasions when it may be useful to have the capability of acquiring a relatively large intact tissue sample. One such core biopsy device is disclosed in U.S. Pat. No. 5,111,828, to Komberg et al., also expressly incorporated by reference herein. In the device disclosed by Komberg et al., the tissue receiving port is disposed at the distal end of the device and is oriented axially rather than laterally. A disadvantage of this type of device, however, is the inability to acquire a tissue sample having a cross-section larger than that of the cannula through which the sample will be removed. Additionally, it is difficult, using such a device, which obtains cylindrical shaped specimens, to determine whether an entire lesion of interest is being removed or whether a further procedure will be necessary. This is particularly true because most lesions of interest are typically spherical in shape, having a diameter of approximately 1 cm. The only way one can tell whether the entire lesion has been removed using the Komberg technique is to remove and examine the specimen, determining whether each of the margins of the specimen is "clean", meaning that there is no evidence of lesion, or "dirty", meaning that lesion is evident right to the edge of the specimen. Of course, if one or more specimen margins is "dirty", it is almost a certainty that a portion of the lesion remains in the patient, and if the biopsy test results on the lesion are positive, a further surgical procedure will be indicated.

It would be desirable, therefore, to have an apparatus and method for isolating a target lesion, with a sufficient border around and beyond the lesion that the likelihood of "clean" margins is relatively high. It would further be advantageous to have an apparatus and method available for initially isolating the entire target lesion, by cutting a swath completely about the lesion to cut off its blood supply, after which a further procedure is undertaken to remove it from the patient's body. This approach would help to minimize the migration of possibly cancerous cells from the lesion to surrounding tissue or bloodstream during the removal procedure.

SUMMARY OF THE INVENTION

The present invention addresses the foregoing problems by providing such an apparatus and method for precisely isolating a target lesion, resulting in a high likelihood of "clean" margins. This advantageously will often result in the ability to both diagnose and treat a malignant lesion with only a single percutaneous procedure, with no follow-up percutaneous or surgical procedure required, while minimizing the risk of migration of possibly cancerous cells from the lesion to surrounding tissue or the bloodstream.

More particularly, in one aspect of the invention, a biopsy instrument is provided for retrieving body tissue, which instrument has a longitudinal axis. The instrument comprises a distal end adapted for entry into a patient's body, a shaft disposed along the axis, and a cutting element disposed along the shaft. The cutting element is actuatable between a radially retracted position and a radially extended position. Advantageously, the instrument is rotatable about its axis in the radially extended position to isolate a desired tissue specimen from surrounding tissue by defining a peripheral margin about the tissue specimen. Once the tissue specimen is isolated, it may be segmented by further manipulation of the cutting element, after which the tissue segments are preferably individually removed from the patient's body through a cannula or the like. Alternatively, the specimen may be encapsulated and removed as an intact piece.

In another aspect of the invention, an instrument is provided for retrieving body tissue, having a longitudinal axis and comprising a distal end adapted for entry into a patient's body. The instrument further comprises an element for encapsulating a tissue specimen so that it may be withdrawn as a single unit from the patient's body. The encapsulating element preferably comprises a plurality of bands disposed along the instrument axis, each of which are actuatable between a radially retracted position and a radially extended position.

In yet another aspect of the invention, a method is disclosed for retrieving a tissue specimen from a patient's body, comprising the steps of inserting an instrument having a distal end, a longitudinal axis, and an axially disposed cutting element, into the patient's body, so that a distal end is disposed in a tissue region from which the tissue specimen is to be taken. The cutting element is radially expanded so that a portion thereof is radially outwardly spaced from the axis of the instrument. Once the cutting element is radially expanded, it is rotated about the axis to cut the tissue and create a peripheral boundary about the tissue specimen, to isolate the tissue specimen from surrounding tissue in the tissue region.

The invention, together with additional features and advantages thereof, may best be understood by reference to the following description taken in conjunction with the accompanying illustrative drawing.

DESCRIPTION OF THE INVENTION

Figure 1:
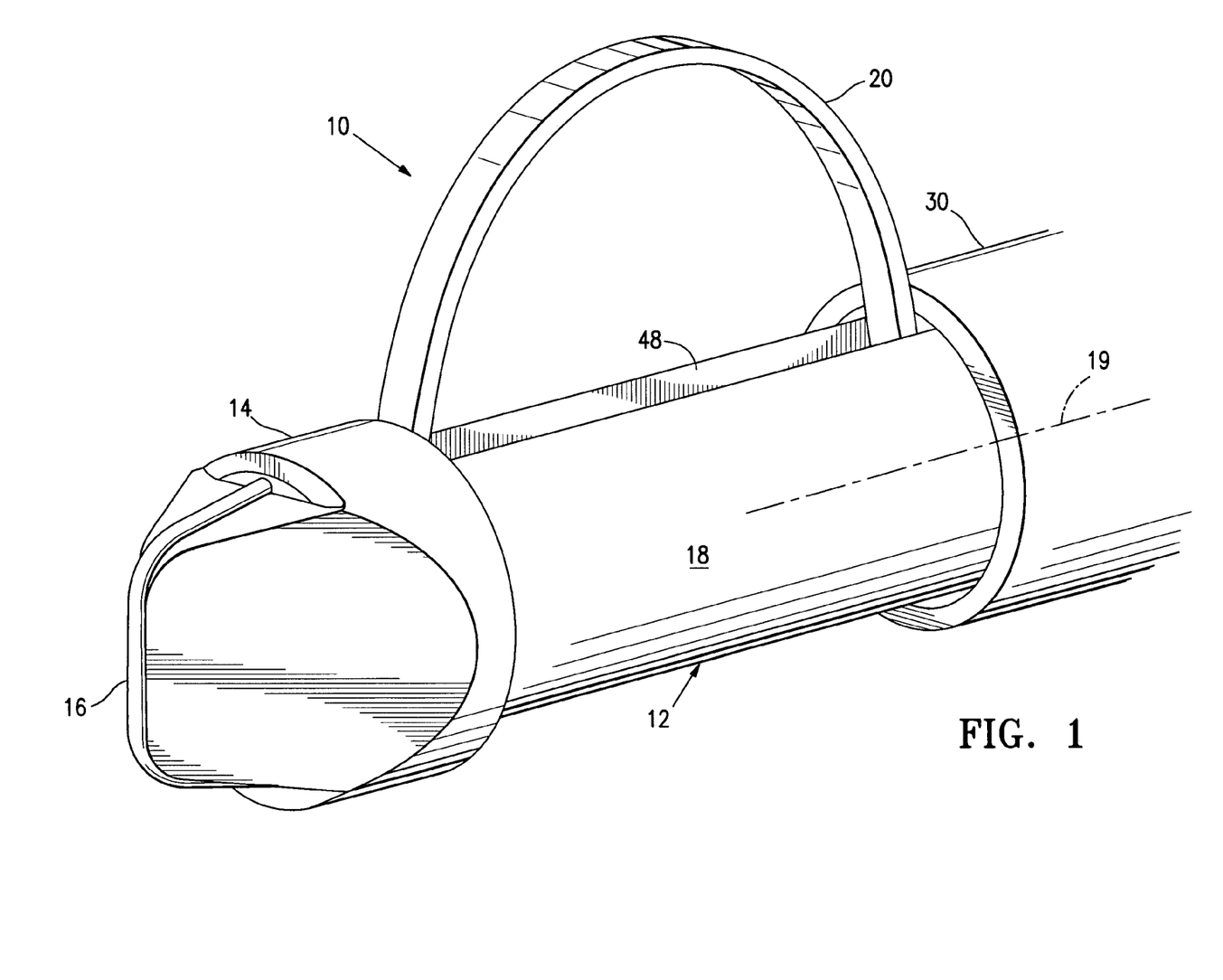
FIG. 1 is a perspective view of the distal end of one preferred embodiment of the inventive tissue retrieval instrument.

Referring now more particularly to FIG. 1, there is shown the distal end 12 of a first preferred embodiment of an inventive tissue retrieval or biopsy instrument 10. The distal end 12 preferably comprises a disposable wand portion, including a distal tip 14. The tip 14 may comprise a conventional trocar tip, or, preferably, may include an electrosurgical (RF) element or wire 16 which may be energized by a conventional electrosurgical generator (not shown) in order to facilitate tissue cutting and consequent advancement of the instrument 10 to a predetermined tissue site in the patient's body.

Proximally of the tip 14 is a shaft 18, preferably lying along an axis 19 (FIG. 1) of the instrument, on which is disposed a cutting element or wire 20. This wire 20 is disposed axially along the length of the shaft 18 in its retracted position (not shown), but may be deployed radially outwardly, as shown in FIG. 1. The element 20 is preferably comprised of a wire or rectangular band fabricated of memory metal such as Nitinol, though stainless steel, tungsten, or other biocompatible materials could also be employed, if desired. The cutting element 20 acts as an electrosurgical cutter, energizable by means of RF energy provided by the electrosurgical generator discussed supra.

Figures 2, 3:
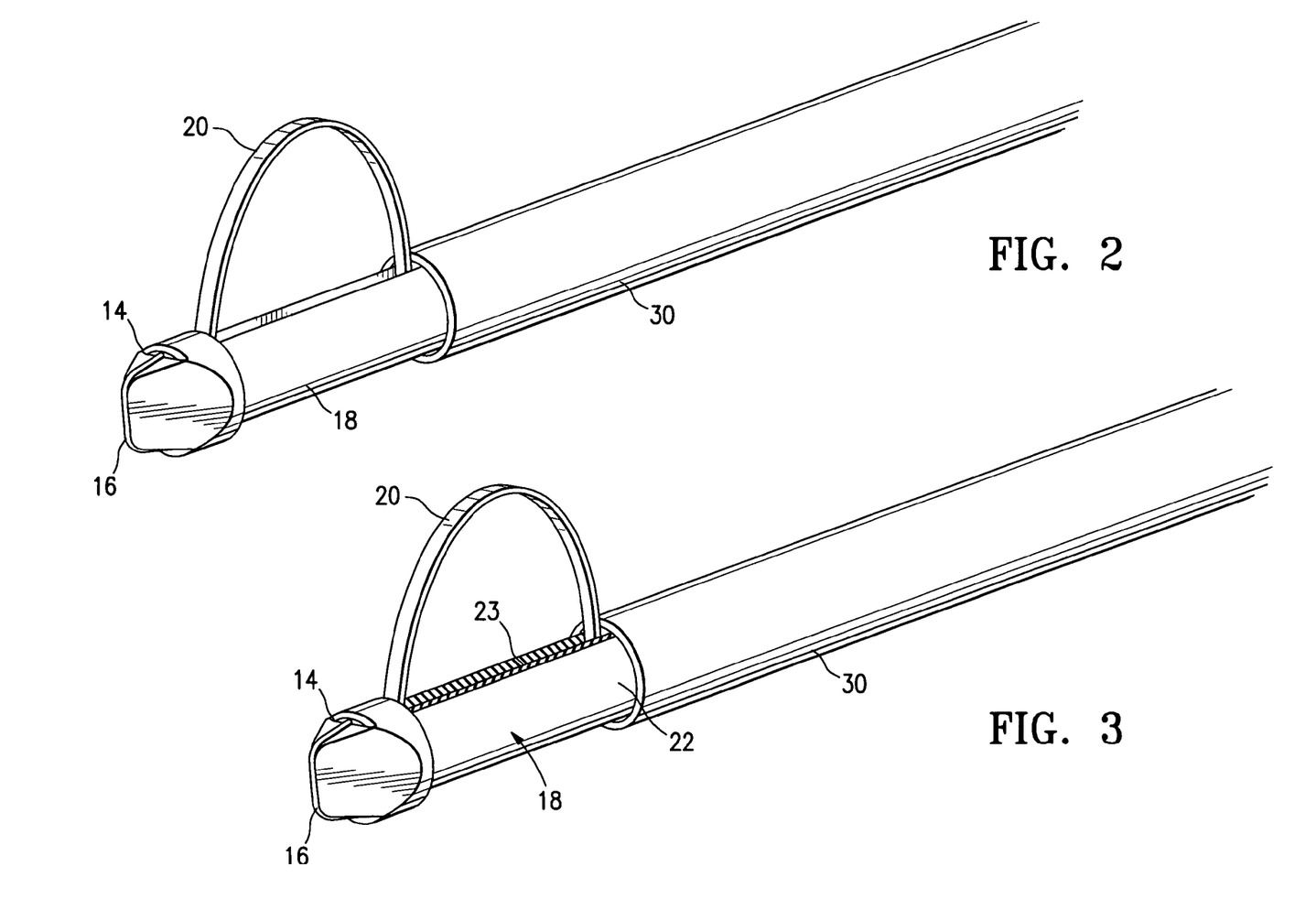
FIG. 2 is a perspective view illustrating the distal end of a monopolar embodiment of the inventive tissue retrieval instrument shown in FIG. 1.
FIG. 3 is a perspective view similar to that of FIG. 2, illustrating the distal end of a bipolar embodiment of the inventive tissue retrieval instrument shown in FIG. 1.
Figure 4:
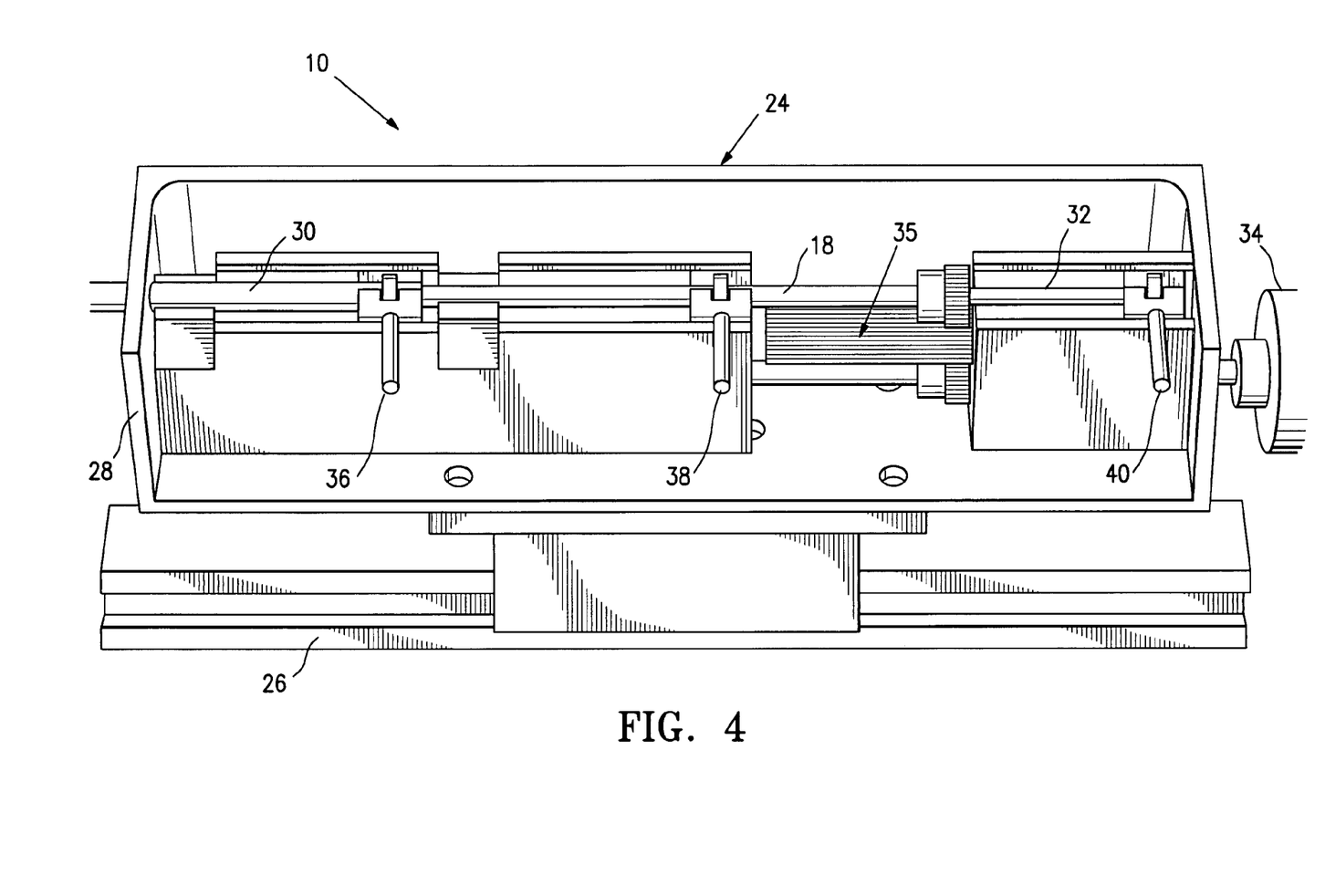
FIG. 4 is a cutaway view from the side illustrating the internal construction of a presently preferred proximal drive unit for operating the inventive tissue retrieval instrument.

The instrument 10 may be monopolar, as illustrated in FIG. 2, with the cutting element 20 comprising the active electrode and a return electrode spaced from the instrument 10 and most typically being disposed on the patient's skin in the form of a patch electrode on the thigh or back. Alternatively, the instrument 10 may preferably be bipolar, as illustrated in FIG. 3, with the cutting element comprising the active electrode and a return electrode 22 being disposed on the instrument in close proximity to the active electrode, such as along the shaft 18. With such an arrangement, a layer of insulation 23 is disposed between the return electrode (comprising a major portion of the surface area of the shaft 18) and the portion of the shaft adjacent to the active electrode, which receives the cutting element 20 in its retracted position. The bipolar embodiment is generally preferred because of a greater safety factor and lower power requirements.

A plurality of cutting wires 20 may be employed if desired, preferably spaced circumferentially about the shaft 18. In some embodiments, it may be preferably to have webs between the cutting elements, to create a "sail" rather than entire distinct separate cutting elements.

Referring now more particularly to FIGS. 4-7, a proximal reusable driver portion 24 for the distal end or disposable wand portion 12 is shown. The driver portion 24 is preferably disposed on a stereotactic rail 26, in known fashion, for guidance of the instrument 10 to a predetermined tissue site using known imaging techniques. Such stereotactic imaging systems are available, for example, from Fischer, Inc. or Lorad, Inc. Alternative imaging systems, such as mammographic, ultrasonic, CT, MRI guidance systems may be used in place of a stereotactic system, if desired. Additionally, the instrument may be guided to the lesion site using an articulating arm system or manually, rather than on a stereotactic rail.

The reusable driver portion 24 comprises a housing 28 within which is disposed a coaxial arrangement comprising an outer sheath 30, the shaft 18, and a rod 32 which is attached at its distal end to the cutter element 20. A knob 34 is rotatably attached to the shaft 18 through a gearing system 35 to rotate the shaft 18 as desired, for the purpose of circumferentially orienting and rotating the cutting element 20. Three levers 36, 38, and 40 extend outwardly through slots 42, 44, and 46, respectively, in the side of the housing 28. The first lever 36 is actuatable to slide the sheath 30 axially both proximally and distally, for a purpose to be described hereinbelow. The second lever 38 is actuatable to move the shaft 18 axially in distal and proximal directions, as desired. The third lever 40 is actuatable to move the rod 32 axially in distal and proximal directions, as desired. Since the rod 32 is attached at its distal end to the proximal end of the wire cutter 20, movement of the rod 32 in an axial direction also causes the proximal end of the wire cutter 20 to move in an axial direction. Since the distal end of the cutter 20 is anchored to the shaft 18, movement of the proximal end of the cutter element 20 in a distal direction causes the midportion of the cutting element 20 to bow radially outwardly to a radially expanded position, as shown in any of FIGS. 1-3, while movement of the proximal end of the cutter element 20 in a proximal direction causes the midportion of the cutter element 20 to retract radially to its stowed position, disposed linearly along the axial length of the shaft 18, preferably within a recess 48 (FIG. 1).

Figure 5:
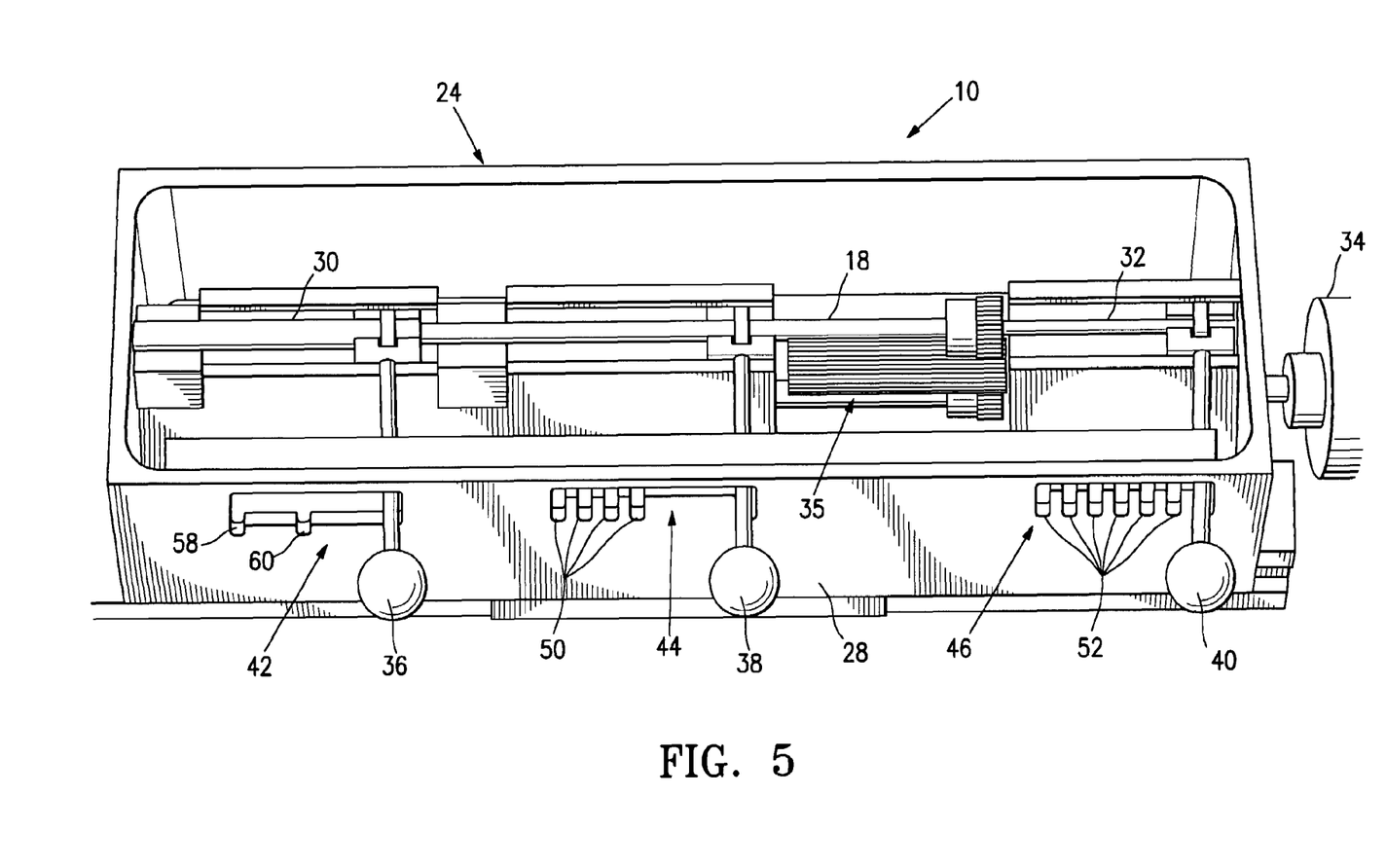
FIG. 5 is a perspective view from the top illustrating the proximal drive unit of FIG. 4, with the top portion of the housing removed in order to show portions of its internal construction.
Figure 6:
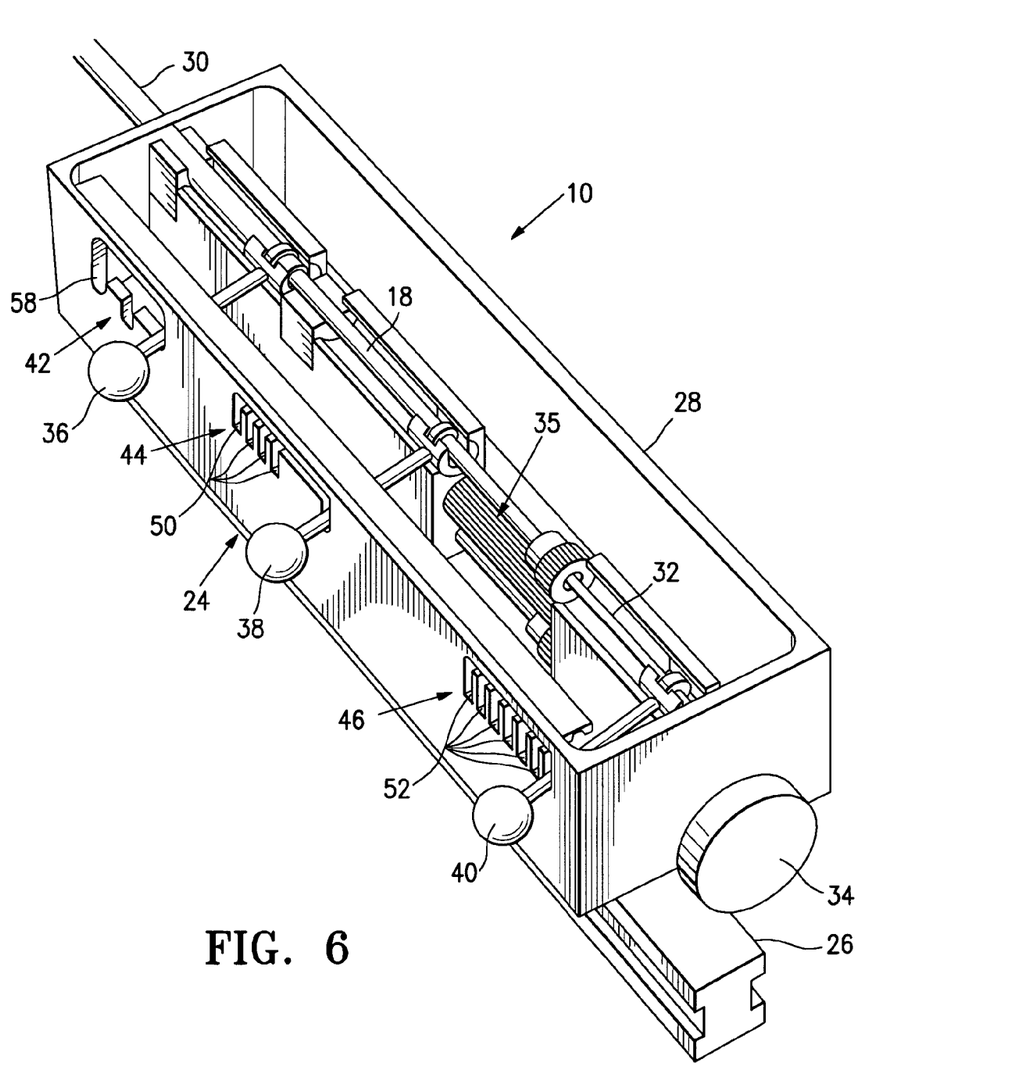
FIG. 6 is a perspective view from the proximal end illustrating the proximal drive unit of FIGS. 4 and 5, with the top portion of the housing removed in order to show portions of its internal construction.
Figure 7:
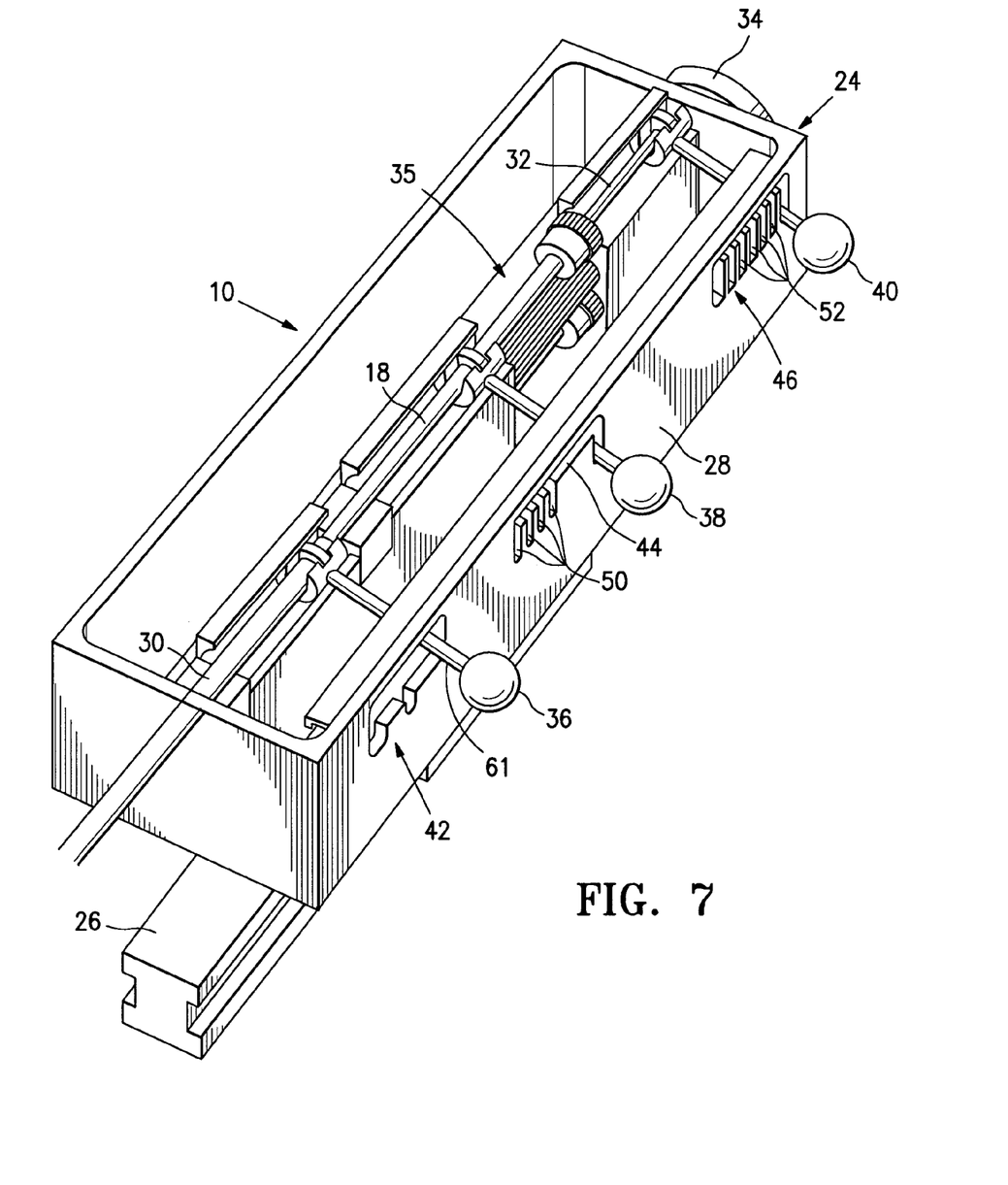
FIG. 7 is a perspective view from the distal end illustrating the proximal drive unit of FIGS. 4-6, with the top portion of the housing removed in order to show portions of its internal construction.

An advantageous feature of the invention is the employment of a series of stops 50 in the second slot 44, and a series of stops 52 in the third slot 46, as illustrated in FIGS. 5-7. The stops 50 enable the second lever 38 to be actuated to a plurality of discrete axial positions, which in turn permits the shaft 18 to be actuated to a corresponding plurality of discrete axial positions for fine tuning the axial position of the electrosurgical cutting element 20. Similarly, the stops 52 enable the third lever 40 to be actuated to a plurality of discrete axial positions, which in turn permits the electrosurgical cutting element 20 to be radially extended to a corresponding plurality of radially extended positions, for a purpose to be described more fully hereinbelow.

Figure 8:
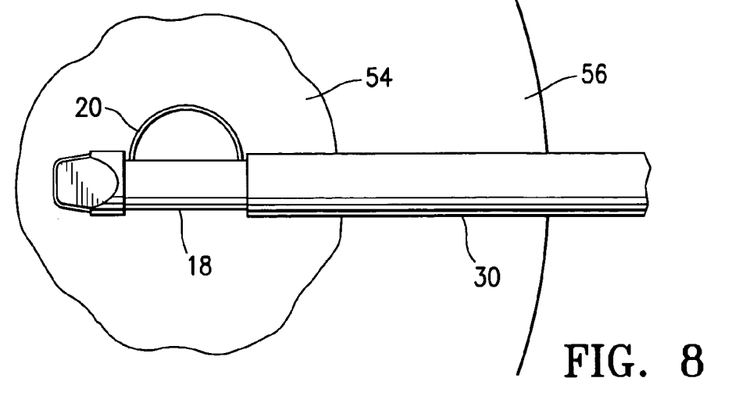
FIG. 8 is a schematic view illustrating the distal end of the instrument of FIG. 1 disposed in a tissue region from which target tissue is to be retrieved, wherein the distal cutting element is deployed in a first position for isolating a first segment of a target tissue specimen from surrounding tissue.
Figure 9:
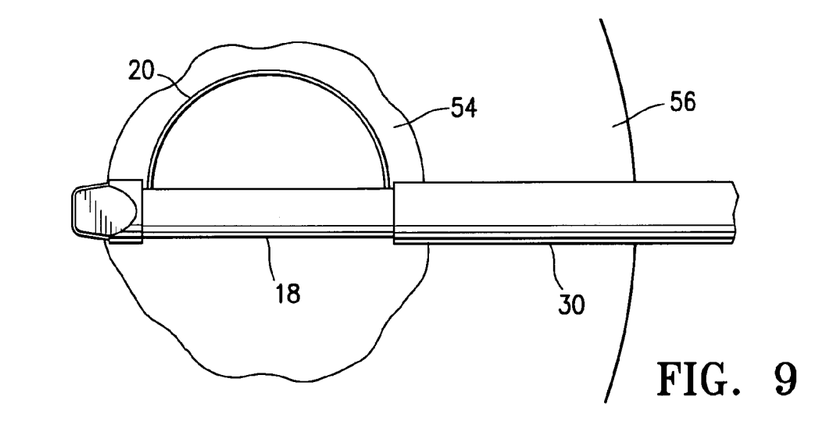
FIG. 9 is a schematic view similar to FIG. 8, wherein the distal cutting element is deployed in a second position for isolating a second segment of the target tissue specimen from surrounding tissue.
Figure 10:
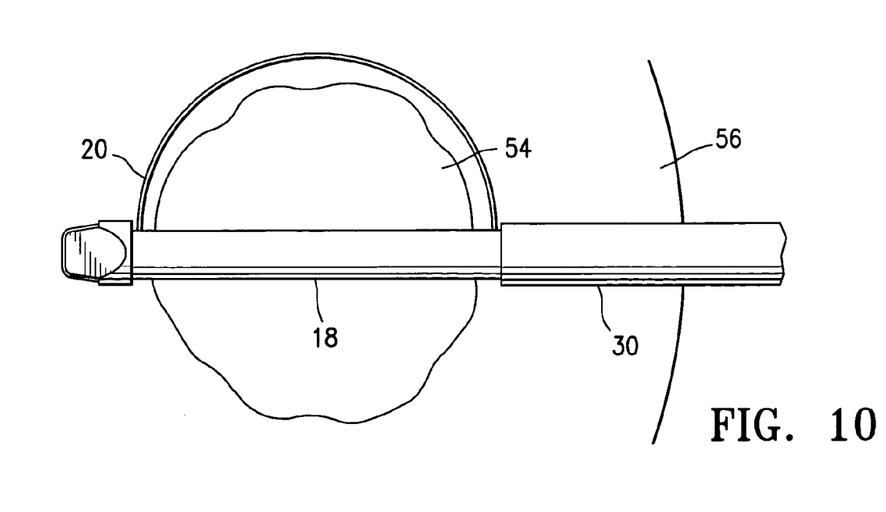
FIG. 10 is a schematic view similar to FIGS. 8 and 9, wherein the distal cutting element is deployed in a third position for isolating a third segment of the target tissue specimen from surrounding tissue.
Figure 11:
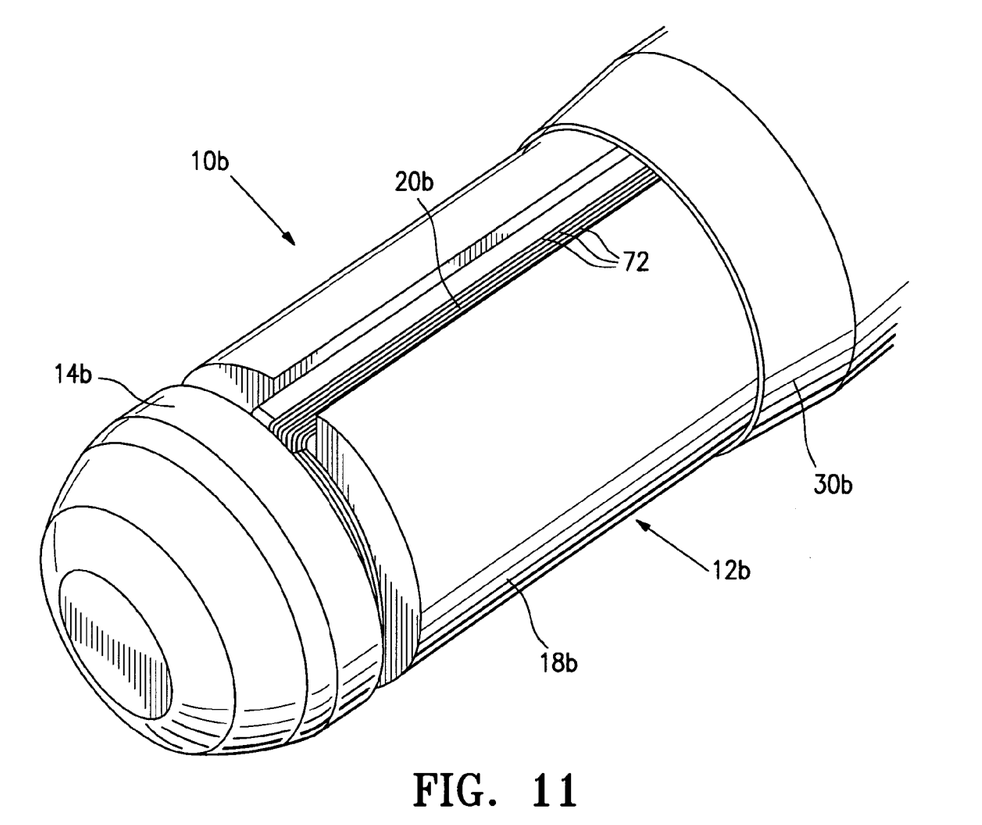
FIG. 11 is a perspective view illustrating the distal end of a second preferred embodiment of the inventive tissue retrieval instrument.
Figure 12:
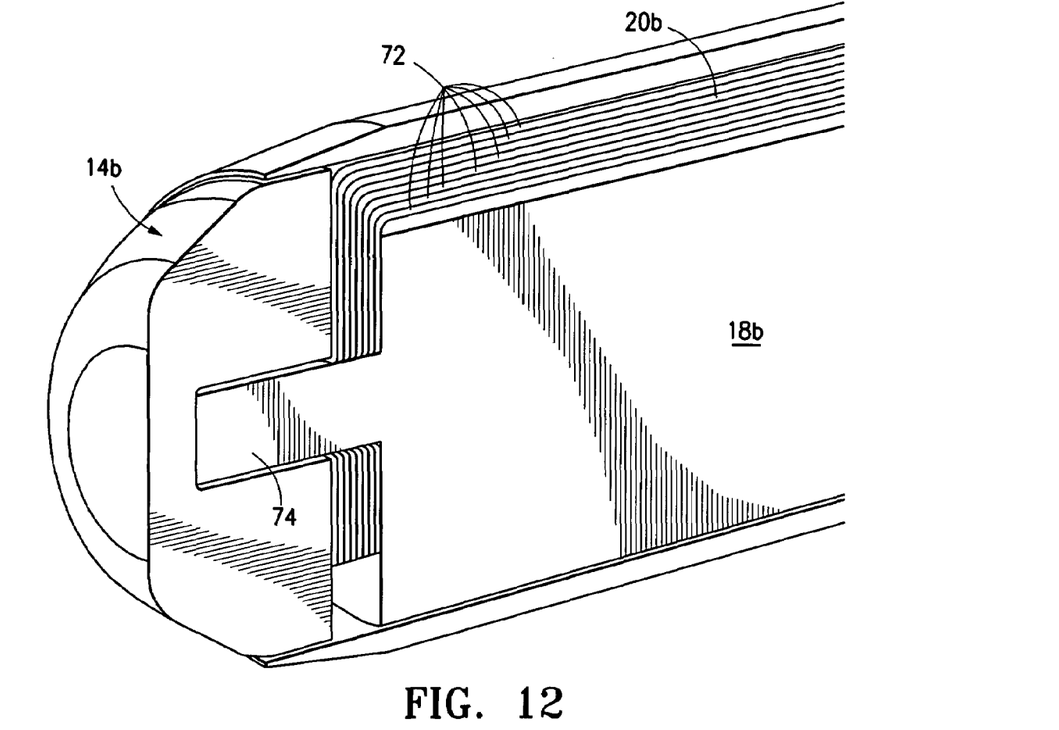
FIG. 12 is a perspective cutaway view of the distal end of the embodiment of FIG. 11, illustrating the internal construction thereof, including tissue wrapping and cutting elements in their stored position.
Figure 13:
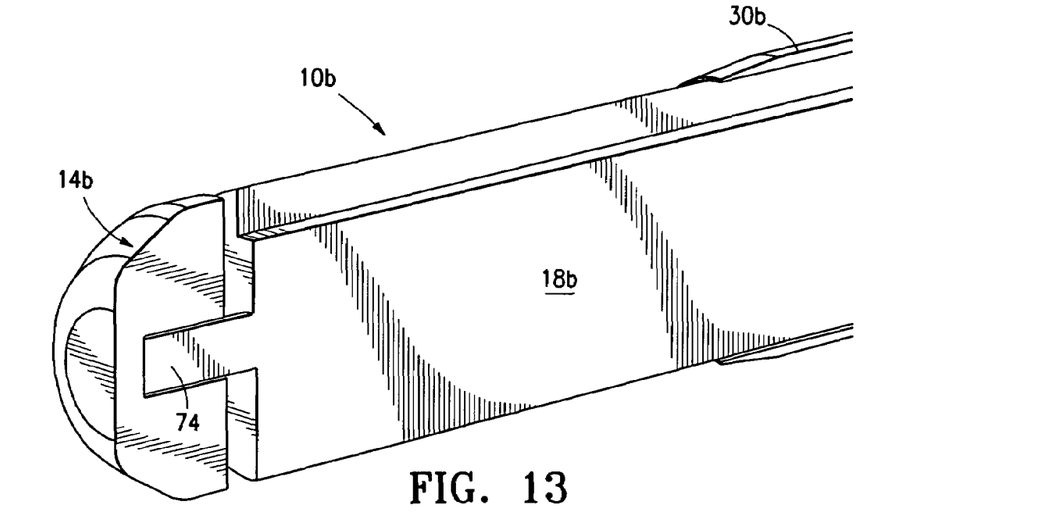
FIG. 13 is a perspective cutaway view similar to that of FIG. 12, wherein the sheath has been retracted in order to deploy the tissue wrapping and cutting elements shown in FIG. 12.

With reference now more particularly to FIGS. 8-10, the operation of the first preferred embodiment of the inventive device will be explained. Initially, when it is determined that either a diagnostic or therapeutic biopsy procedure is indicated, the distal disposable wand portion 12 of the instrument 10 will be moved axially to a position wherein the distal tip is adjacent to and preferably within a target lesion 54, using the stereotactic rail 26 and associated imaging system. During this process step, wherein gross linear movement of the wand 12 is controlled by the rail system 26, the electrosurgical cutting element 16 on the distal tip 14 is energized to pierce and cut through the patient's body tissue 56 to permit distal advancement of the wand 12 to the region surrounding the lesion 54.

Once the distal tip 14 is generally in the desired position adjacent to or within the target lesion 54, using the stereotactic rail 26, the second lever 38 is actuated to provide fine tuning of the axial position of the distal tip 14 relative to the lesion 54, by moving the shaft 18 axially to a desired position, and securing the lever 38 in an appropriate stop 50 to maintain the desired axial position. This fine axial adjustment of the axial movement of the shaft 18 is performed using appropriate imaging equipment. The objective of this process step is to ensure that the distal end of the cutting wire 20 is disposed distally of the distal peripheral edge of the lesion 54, while at the same time the proximal end of the cutting wire 20 is disposed proximally of the proximal peripheral edge of the lesion 54. This will ensure the ability to isolate the entire lesion 54 during the cutting procedure, with sufficient margins to minimize the chance that any portion of the lesion inadvertently remains behind in the patient's body following removal thereof.

When the distal tip 14 is in the precise position desired by the practitioner, first lever 36, which is normally disposed in a first detent 58 (FIGS. 5 and 6) in the first slot 42, is actuated proximally until it rests in a second detent 60 (FIG. 5) in the first slot 42. This action retracts the sheath 30 proximally a sufficient distance to partially uncover the cutting element 20. It should be noted, however, that in some circumstances it may be desirable to fully retract the sheath, so that the entire cutting element 20 is released, in order to create a different cutting geometry. In such an instance, a detent 61 (FIG. 7) is provided within the slot 42 to accommodate the lever 36 in the fully proximal position necessary to achieve full axial retraction of the sheath. Additional intermediate detents 60 (not shown) may be provided to retract the sheath to intermediate positions corresponding to various partial radial extension positions of the cutting element.

After the sheath 30 is retracted as desired, the third lever 40 may then be actuated distally along the third slot 46 to an intermediate stop 52, thereby causing the rod 32, and therefore the proximal end of the cutting element 20, to move axially a distance equivalent to that traversed by the lever 40. This, of course, results in the partial radial expansion of the cutting element 20 to an arched or bowed configuration as shown in FIG. 8. The extended configuration of the cutting element 20 may define, when rotated about the instrument axis, a spherical cutting volume, as shown, or it may be configured to define an elliptical or toroidal cutting volume when the cutting element is rotated about the instrument axis 19, rather than a spherical volume.

Of course many other mechanisms for radially expanding the cutting element 20 may be utilized as well, within the scope of the invention. For example, since the wire 20 is preferably fabricated of a shaped memory or superelastic material, the proximal retraction of the sheath 30, and resultant release of the wire 20, may be sufficient to cause the cutting wire 20 to radially expand to its desired position.

Once the cutting element 20 is partially radially expanded as described supra, an inner portion of the target lesion 54 is isolated from surrounding tissue. To complete this step, the cutting element 20 is energized by the electrosurgical generator (not shown), after which the knob 34 is rotated, either manually or via a motorized drive mechanism, to rotate the cutting element 20 through a 360 degree arc. This rotational cutting action functions to completely sever the inner portion of the tissue sample from the surrounding tissue, thereby cutting off all blood supply to the inner tissue sample. Alternatively, if desired, the cutting element 20 may be simultaneously rotated and moved axially, by moving the shaft 18 axially, in order to create a "corkscrew"-shaped tissue segment.

Once this initial isolation step is completed, the cutting element or wire 20 is preferably further radially extended to the position shown in FIG. 9. This is accomplished by sliding the lever 36 proximally to another detent 60 to further proximally retract the sheath 30. Then, the third lever 40 may be axially slid distally to another stop or detent 52 to further radially extend the cutting wire 20. Once radially positioned, the cutting element 20 is energized by the electrosurgical generator, after which the knob 34 is rotated to rotate the cutting element 20 through a 360 degree arc. This rotational cutting action functions to completely sever a second segment of the tissue sample from the surrounding tissue, thereby cutting off all blood supply to this segment as well.

These steps may be repeated as many times as desired, in order to ensure that the tissue sample is segmented for efficient removal from the patient's body. Ultimately, however, a final cut is preferably made, by fully retracting the outer sheath 30, using the slide lever 36, and fully extending the cutting wire 20, using the slide lever 40, so that the cutting element 20 extends radially beyond the periphery of the target lesion 54, as illustrated in FIG. 10. The cutting element is then energized with RF energy, in the same manner as previously, after which the knob 34 is rotated to rotate the cutting wire 20 through a complete arc about the axis 19. At this point, the entire lesion 54 should be completely isolated from surrounding tissue, with a sufficient margin about the outer periphery thereof to ensure successful removal of the entire lesion.

During the foregoing segmentation process, if the cutting element 20 remains charged by RF energy during the stepwise radial extension process, the outer tissue rings will be further segmented radially.

Other segmentation approaches may be advantageously utilized as well, if desired. For example, rather than segmenting the tissue sample circumferentially, from the inside out, the tissue sample may be segmented circumferentially from the outside in, i.e. by making an outer circumferential cut (FIG. 10), then partially retracting the cutting element 20 and cutting additional layers, as shown in FIGS. 8 and 9. Alternatively, the tissue may be sectioned by extending and retracting the cutting element 20 radially, akin to "sectioning an orange". Additional radially oriented cutting elements could be employed as well to further segment the tissue.

Figure 17:
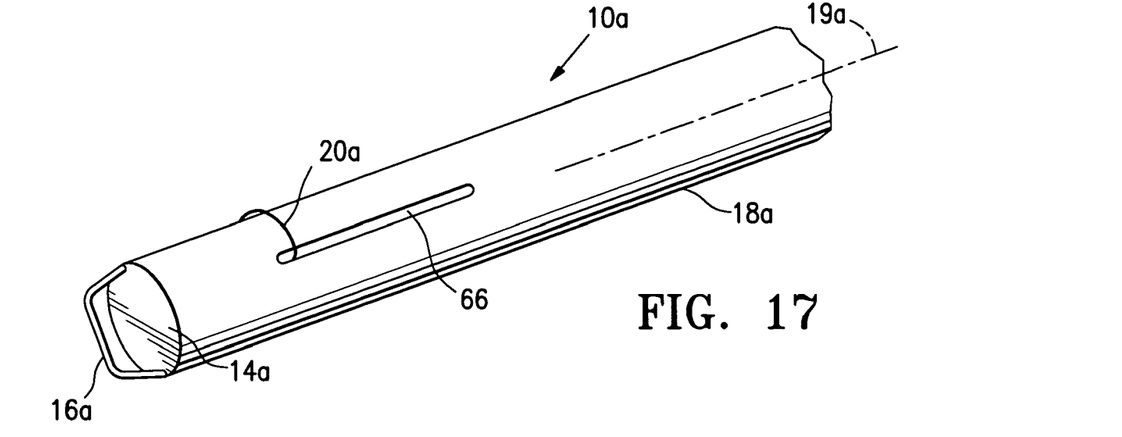
FIG. 17 is a perspective, schematic view of an alternative embodiment of the distal end of the inventive tissue retrieval instrument, wherein the cutting element of the instrument is in a retracted position.
Figure 18:
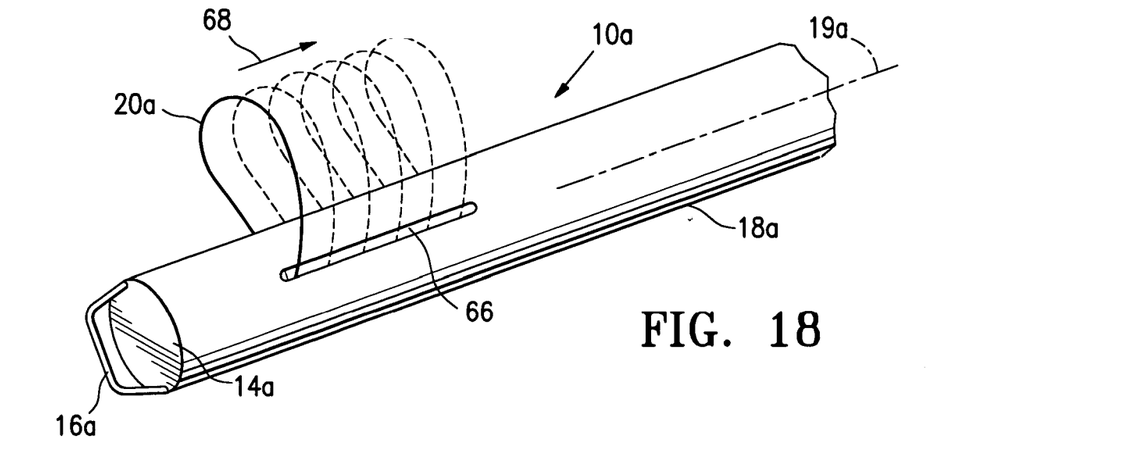
FIG. 18 is a perspective, schematic view similar to FIG. 17, illustrating the cutting element in a deployed position for creating cylindrical tissue segments.
Figure 19:
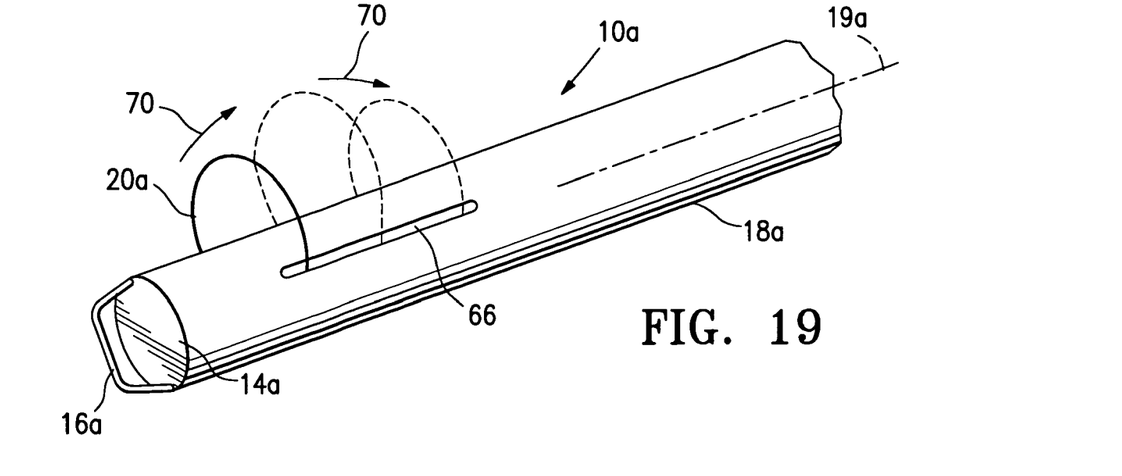
FIG. 19 is a perspective, schematic view similar to FIGS. 17 and 18, illustrating the cutting element in a deployed position for creating tissue segments of varying heights.

An alternative approach to segmenting the tissue specimen to be retrieved is illustrated in the embodiment shown in FIGS. 17-19. In this embodiment, wherein like elements to those in the embodiment of FIG. 1 are designated by like reference numerals, succeeded by the letter a, there is shown a tissue retrieval or biopsy instrument 10a, having a distal tip 14a with an electrosurgical element or wire 16a for cutting tissue and thereby permitting advancement of the instrument into a patient's body. A shaft or cannula 18a is disposed along an axis 19a of the instrument. A longitudinal slot 66 is disposed axially along a portion of the length of the cannula 18a. A cutting element or wire 20a, which is preferably an electrosurgical cutting element, is disposed so as to be extendable from and retractable into the slot. The cutting element is shown in a retracted position in FIG. 17, and in an extended position in FIGS. 18 and 19.

In operation, once the instrument 10a has been positioned so that the distal tip is adjacent to a lesion to be removed, in the manner described supra with respect to the embodiment of FIG. 1, the cutting element 20a is charged with RF energy from a proximally disposed electrosurgical generator (not shown). Then, the cutting element 20a is radially extended by the practitioner, using a proximal control mechanism (not shown), to a position as shown, for example, in FIG. 18. Once extended, the cutting element is moved axially in a proximal direction along the slot 66, as illustrated by the arrow 68 and the phantom images of the cutting element 20a, in order to isolate a generally cylindrical tissue segment, as the cannula 18a is rotated about its axis 19a simultaneously.

FIG. 19 illustrates a procedure similar to that illustrated in FIG. 18, except that while the cutting element 20a is being axially moved in a proximal direction as shown by arrows 70, it is also deployed to various radial heights, in order to create a variable height cut.

Once segmentation of the tissue sample has been completed, whichever embodiment has been employed, each tissue segment can be withdrawn using a suitable retrieval apparatus. Preferably, the tissue segments are withdrawn through a cannula, such as the sheath 30, using such means as a suction grasper, flexible mechanical graspers, an auger conveyor, a prickly bristle or brush grasper, a wire retrieval basket, or the like.

The foregoing procedure and apparatus may be used for either a diagnostic or a therapeutic purpose. It is particularly advantageous for a diagnostic procedure because the resultant incision from the procedure will not substantially exceed in length the diameter of the cannula. On the other hand, a second preferred embodiment, illustrated in FIGS. 11-16, is particularly suited to a therapeutic procedure, wherein it is highly desired to ensure that the entire lesion of interest is removed in one step, without segmenting that lesion within the body. This approach emphasizes maximum safety, in that only a single procedure is necessary, assuming the tissue sample margins are clean, and the incision necessary to remove the intact tissue sample is of the minimum size necessary to remove the sample. With this procedure, there is also a somewhat reduced risk of cell migration from the specimen to the surrounding tissue, since as described below, the specimen is encapsulated as soon as it is isolated and then promptly removed. No segmentation of the specimen occurs within the patient's body.

Referring now to FIGS. 11-14, wherein like elements to those in the first embodiment are identified by like reference numerals, followed by the letter "b", there is shown the distal end or disposable wand portion 12b of an instrument 10b. The portion 12b includes a distal tip 14b, which may be constructed in a manner similar to that of tip 14 in FIG. 1, a shaft 18b, and a sleeve 30b. Disposed in a radially retracted orientation in a recess 48b of the shaft 18b are a plurality of encapsulation elements or bands 72, one of which also comprises a single electrosurgical cutting element 20b. For the purposes of the invention it is unimportant which of the encapsulation elements 72 may be charged by means of RF energy to form an electrosurgical cutter, and in certain instances it may be advantageous to employ a plurality of cutting elements. Each of the encapsulation elements 72 and the cutting element 20b are attached at their distal ends to the distal end of the shaft 18b, at its connection with the distal tip 14b of the instrument 10b, which connection is preferably accomplished by means of a keyway 74.

Figure 14:
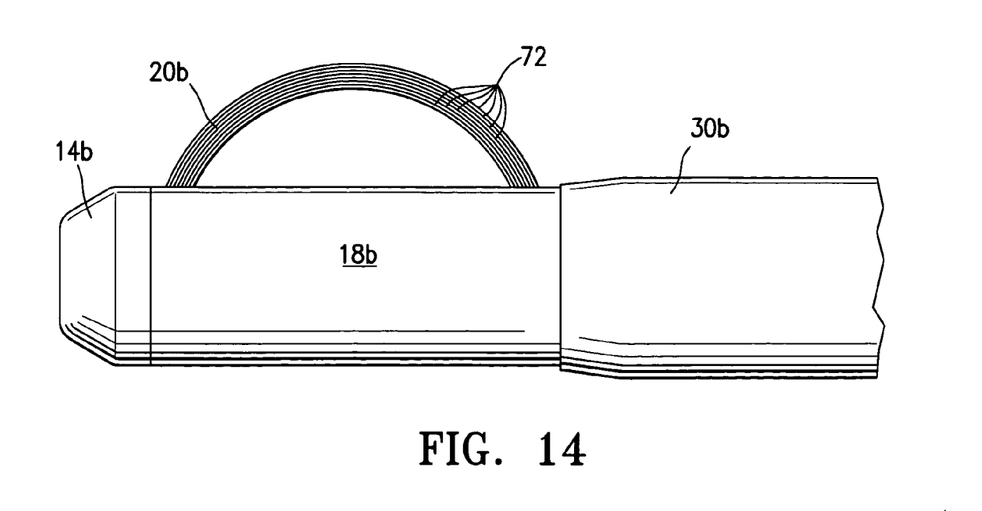
FIG. 14 is a side schematic view of the distal end of the embodiment of FIGS. 11-13, illustrating the deployment of the tissue wrapping and cutting elements shown in FIG. 12.
Figure 15:
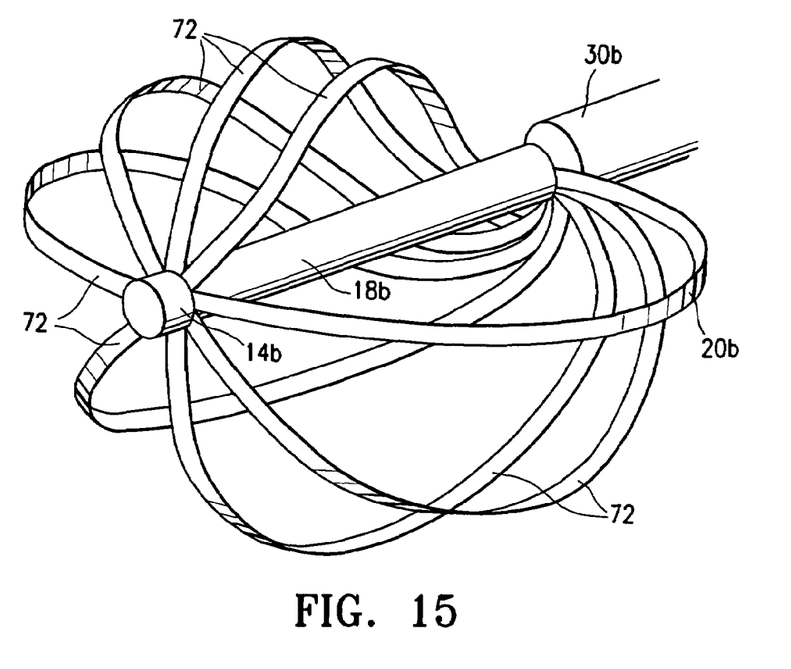
FIG. 15 is a perspective view illustrating the tissue wrapping and cutting elements of FIGS. 12 and 14 in their fully deployed position.
Figure 16:
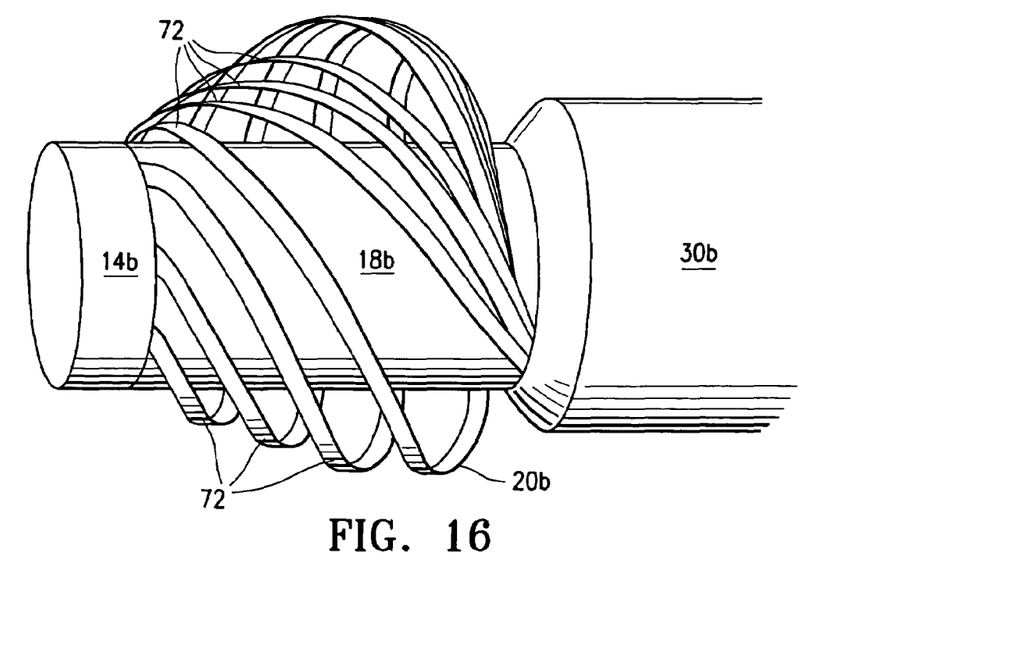
FIG. 16 is a side view showing the deployed tissue wrapping and cutting elements after the distal end of the instrument has been rotated to twist the wrapping and cutting elements in order to wrap a target tissue sample.

The proximal end of the instrument 10b may be substantially the same as that for the instrument 10, illustrated in FIGS. 4-7, comprising a reusable driver portion having an actuator for axially moving the sheath 30b between proximal and distal positions, a linear actuator for axially moving the shaft 18b, an actuator for rotationally moving the shaft 18b, and an actuator for axially moving the proximal ends of the encapsulation elements 72 and cutting element 20b, in order to radially extend and retract each of the elements 72 and 20b, as illustrated in FIGS. 14-16.

In operation, as with the first embodiment of FIG. 1, when it is determined that either a diagnostic or therapeutic biopsy procedure is indicated, the distal disposable wand portion 12b of the instrument 10b will be moved axially to a position wherein the distal tip is adjacent to and distally of a target lesion, using the stereotactic rail 26 and associated imaging system. During this process step, wherein gross linear movement of the wand 12b is controlled by the rail system 26, the electrosurgical cutting element (not shown) on the distal tip 14b is energized to pierce and cut through the patient's body tissue to permit distal advancement of the wand 12b to the region surrounding the lesion.

Once the distal tip 14b is generally in the desired position adjacent to the target lesion, using the stereotactic rail 26, the second lever 38 is actuated to provide fine tuning of the axial position of the distal tip 14b relative to the lesion, by moving the shaft 18b axially to a desired position, and securing the lever 38 in an appropriate stop 50 to maintain the desired axial position. This fine axial adjustment of the axial movement of the shaft 18b is performed using appropriate imaging equipment. The objective of this process step is to ensure that the distal end of the cutting wire 20b is disposed distally of the distal peripheral edge of the lesion, while at the same time the proximal end of the cutting wire 20b is disposed proximally of the proximal peripheral edge of the lesion. This will ensure the ability to isolate the entire lesion during the cutting procedure, with sufficient margins to minimize the chance that any portion of the lesion inadvertently remains behind in the patient's body following removal thereof.

When the distal tip 14b is in the precise position desired by the practitioner, first lever 36, which is normally disposed in a first detent 58 (FIGS. 5 and 6) in the first slot 42, is actuated proximally until it rests in a second detent 60 (FIG. 7) in the first slot 42. This action retracts the sheath 30b proximally a sufficient distance to completely uncover the cutting element 20b and associated encapsulation elements 72. The third lever 40 may then be actuated distally along the third slot 46 to the distal-most stop 52, thereby causing the rod 32, and therefore the proximal ends of the cutting element 20a and encapsulation elements 72, to move axially a distance equivalent to that traversed by the lever 40. This, of course, results in the radial expansion of the cutting element 20b and encapsulation elements 72 to an arched or bowed configuration as shown in FIG. 14, wherein the cutting element 20b defines a peripheral boundary which lies radially beyond the peripheral boundary of the lesion, as in the case of the first embodiment shown in FIG. 8. Again, it should be noted that the cutting element and encapsulation elements need not be fully extended, especially if an ellipsoidal or toroidal cutting geometry is desired, in which case intermediate stop 61 is utilized.

Once the cutting element 20b and associated encapsulation elements 72 are radially expanded as described supra, it is time to isolate the target lesion from surrounding tissue. Advantageously, a spherical or toroidal tissue sample having a radius of at least 15 mm may be defined and isolated by rotating the cutting element 20b about the axis of the shaft 18b. The encapsulation elements 72 will also be rotated during this process, but their function is not yet important. To complete the isolation step, the cutting element 20b is energized by the electrosurgical generator (not shown), after which the knob 34 is rotated, either manually or via a motorized drive mechanism, to rotate the shaft 18b, and thus the cutting element 20b through a 360 degree arc. This rotational cutting action functions to completely sever the tissue sample from the surrounding tissue, thereby cutting off all blood supply to the tissue sample (and thus from the lesion, which should be completely contained within the tissue sample).

After the isolation step is completed, the isolated tissue sample may be retrieved from the patient's body 56. This retrieval step may be accomplished in a number of ways, but it is the objective in connection with the illustrated embodiment to encapsulate and remove the isolated tissue sample in one piece. Accordingly, as is illustrated in FIGS. 15 and 16, continued rotation of the shaft 18b, once the isolation step has been completed, preferably with the cutting element 20b de-energized, will twist and tighten the encapsulating elements 72 and the cutting element 20b about the tissue sample (not shown). As the shaft 18b is rotated, and the encapsulating elements 72 radially retracted and twisted, they will function to deform the tissue sample radially so that it is more compact and more securely retained within the spaced defined by the encapsulating elements 72.

Once the tissue sample has been fully encapsulated, the tissue sample may be removed from the patient's body. Advantageously, since the tissue sample is larger in cross-section than the cross-section of the sheath 30b, the inventors have developed an inventive approach for removal thereof which results in minimum trauma and incision size for the patient while still permitting the removal of an intact specimen. To remove the specimen, the sheath 30b is retracted proximally, following which the cutting element 20b is again energized by the electrosurgical generator. The shaft 18b, with the tissue specimen encapsulated thereabout, is then proximally withdrawn by the practitioner, with the cutting element 20b functioning to cut through the tissue necessary to create a passage for exit of the sample. Once the unit, including the shaft and encapsulated tissue mass, is completely withdrawn from the body, the incision created by the cutting element 20b upon withdrawal from the body may be adhesively closed, with minimal required follow-up care and scarring.

Many alternative embodiments may be used to accomplish the method outlined supra, which essentially involves isolating the tissue mass from surrounding tissue, encapsulating the tissue mass in place about a shaft, then removing the encapsulated tissue mass and shaft from the body by energizing an RF electrosurgical cutter to cut its way out, without the need for a cannula or pre-existing incision. For example, a plurality of cutting elements could be employed, or a separate cutting element could be disposed on the shaft. An important aspect of the invention, of course, is a relatively high likelihood of acquiring the entire lesion of interest in a single therapeutic procedure, without the need for follow-up surgery.

While this invention has been described with respect to various specific examples and embodiments, it is to be understood that the invention is not limited thereto and that it can be variously practiced within the scope of the following claims.

What is claimed is:

1. A biopsy instrument for retrieving body tissue at an intracorporeal site, having a longitudinal axis and comprising:
   an elongated shaft having a distal shaft portion and a distal end having a tissue cutting surface adapted for passage throuh tissue in a patient's body to the intracorporeal site; and
   an electrosurgical cutting element longitudinally disposed on the distal shaft portion of said instrument proximal to the distal end, which is actuatable between a radially retracted position and a radially extended position, relative to said axis, and being rotatable in said radially extended position while energized with RF electrical enerqy to separate a desired tissue specimen from surrounding tissue by defining a peripheral margin about said tissue specimen.

2. The biopsy device of claim 1 wherein the first electrosurgical tissue cutting element is rotatable at least in part about the longitudinal axis independent of the distal tip when energized by RF electrical energy.

3. A biopsy device for isolating one or more tissue specimens from an intracorporeal site within a patient's body, comprising:
   a. an elongated shaft having proximal and distal ends, a longitudinal axis and a housing on the proximal end;
   b. a distal tip on the distal end having a tissue cutting surface configured for penetration through tissue of the patient's body to gain access to the intracorporeal site therein;
   c. a first electrosurgical tissue cutting element which is longitudinally disposed on a distal portion of the elongated shaft proximal to the distal tip, which is expandable from a retracted position to a radially extended position relative to the longitudinal axis, and which is movable in the radially extended position when powered by RF energy to isolate a tissue specimen from surrounding tissue at the intracorporeal site; and
   d. an electrical conductor which is configured to electrically interconnect the proximal electrosurgical tissue cutting element with a source of RF energy.

4. The biopsy device of claim 3 wherein the tissue cutting surface on the distal tip is a second electrosurgical tissue cutting element secured thereto which is energized with RF electrical energy to facilitate penetration of tissue to the intracorporeal site.

5. The biopsy device of claim 4 wherein the second electrosurgical tissue cutting element secured to the distal tip of the shaft has a curvilinear cutting surface.

6. The biopsy device of claim 4 wherein the second electrosurgical tissue cutting element secured to the distal tip is a monopolar electrode.

7. The biopsy device of claim 4 wherein the second electrosurgical tissue cutting element secured to the distal tip is a bipolar electrode.

8. The biopsy device of claim 4 wherein an electrical conductor is secured to the second electrosurgical tissue cutting element and is configured to transmit RF electrical energy to the second electrosurgical tissue cutting element.

9. The biopsy device of claim 4 wherein the second electrosurgical tissue cutting element is in part distally spaced away from the distal tip.

10. The biopsy device of claim 3 the first electrosurgical tissue cutting element comprises a monopolar electrode.

11. The biopsy device of claim 3 wherein the first electrosurgical tissue cutting element comprises a bipolar electrode.

12. The biopsy device of claim 3 wherein the first electrosurgical tissue cutting element has a distal end secured to the elongated shaft and a proximal end which is configured to be moved longitudinally to radially move the first electrosurgical tissue cutting element to a tissue cutting configuration.

13. The biopsy device of claim 3 wherein the first electrosurgical tissue cutting element is configured to segment a tissue specimen after it has been isolated from the surrounding tissue by energizing the first electrosurgical tissue cutting element as the tissue cutting element is returned to the retracted configuration.

14. The biopsy device of claim 3 wherein the first electrosurgical tissue cutting element is radially expandable to a plurality of radially extended positions.

15. The biopsy device of claim 14 wherein the first electrosurgical tissue cutting element is rotatable at least in part about the longitudinal axis in a plurality of radially extended positions.

16. The biopsy device of claim 3 wherein the elongated shaft has an inner lumen for removing all or part of a tissue specimen from the patient's body.

17. The biopsy device of claim 3, including an outer sheath which is disposed about the elongated shaft.

18. The biopsy device of claim 17 wherein the outer sheath is axially movable between a distal position covering at least in part the first electrosurgical tissue cutting element and a proximal position uncovering at least part of the first electrosurgical tissue cutting element.

19. The biopsy device of claim 3 wherein a driver unit is disposed in the housing for controlling radial expansion and retraction and rotation of the first electrosurgical tissue cutting element.

20. The biopsy device of claim 19 wherein the driver unit further controls axial movement of the shaft and axial movement of said sheath.

21. The biopsy device of claim 3 including at least one encapsulation element.

22. The biopsy device of claim 21 wherein at least one encapsulation element is radially extendable from a radially retracted position to a radially extended position.

23. The biopsy device of claim 3 wherein the first electrosurgical tissue cutting element isolates a desired tissue specimen from surrounding tissue by defining a peripheral margin about at least part of the tissue specimen when the first electrosurgical tissue cutting element is rotated at least in part around the longitudinal axis when electrically connected to a RF electrical power source.

* * * * *